US011479523B2

(12) United States Patent
Raja et al.

(10) Patent No.: US 11,479,523 B2
(45) Date of Patent: Oct. 25, 2022

(54) SINGLE STEP PROCESS FOR THE OXIDATION OF CYCLOHEXANE

(71) Applicant: Council of Scientific & Industrial Research, New Delhi (IN)

(72) Inventors: Thirumalaiswamy Raja, Maharashtra (IN); Shatabdi Porel Mukherjee, Maharashtra (IN); Marimuthu Prabhu, Maharashtra (IN); Yogita Manikroa Shikre, Maharashtra (IN)

(73) Assignee: Council of Scientific & Industrial Research

( * ) Notice: Subject to any disclaimer, the term of this patent is extended or adjusted under 35 U.S.C. 154(b) by 505 days.

(21) Appl. No.: 16/491,713

(22) PCT Filed: Mar. 3, 2018

(86) PCT No.: PCT/IN2018/050112
§ 371 (c)(1),
(2) Date: Sep. 6, 2019

(87) PCT Pub. No.: WO2018/163198
PCT Pub. Date: Sep. 13, 2018

(65) Prior Publication Data
US 2021/0130278 A1    May 6, 2021

(30) Foreign Application Priority Data

Mar. 7, 2017 (IN) .............................. 201711007873

(51) Int. Cl.
*C07C 51/31* (2006.01)
*B01J 37/03* (2006.01)
(Continued)

(52) U.S. Cl.
CPC ............. *C07C 51/313* (2013.01); *B01J 23/34* (2013.01); *B01J 35/02* (2013.01); *B01J 37/031* (2013.01);
(Continued)

(58) Field of Classification Search
CPC ... C07C 51/313; C07C 55/14; C07C 2523/34; B01J 23/34; B01J 37/031; B01J 37/08
See application file for complete search history.

(56) References Cited

U.S. PATENT DOCUMENTS 3,361,806 A   1/1968   Lidov et al.
5,897,945 A * 4/1999   Lieber .................... C30B 23/00
                                              428/323

(Continued)

FOREIGN PATENT DOCUMENTS

CN    105618093 A    6/2016
CN    106179326 A    12/2016

OTHER PUBLICATIONS

Wu, W., et al., The effect of pH value on the synthesis and photocatalytic performance of MnWO4 nanostructure by hydrothermal method, Journal of Experimental Nanoscience, vol. 7, No. 4, pp. 390-398 (Year: 2012).*

(Continued)

*Primary Examiner* — Yate' K Cutliff
(74) *Attorney, Agent, or Firm* — Belles Katz LLC

(57) ABSTRACT

The present invention disclosed a single step process for the conversion of cyclohexane to adipic acid by using manganese oxide, tungsten oxide or Mn—WOx nano structure having improved yield and selectivity.

7 Claims, 6 Drawing Sheets

(51) Int. Cl.
- *B01J 23/34* (2006.01)
- *B01J 35/02* (2006.01)
- *B01J 37/08* (2006.01)
- *C07C 55/14* (2006.01)

(52) U.S. Cl.
CPC ............... *B01J 37/08* (2013.01); *C07C 55/14* (2013.01); *C07C 2523/34* (2013.01)

(56) References Cited

U.S. PATENT DOCUMENTS 5,958,821 A * 9/1999 Ishii .................... B01J 31/2234
548/545
2012/0095258 A1 4/2012 Alshammari et al.

OTHER PUBLICATIONS

International Search Report and Written Opinion from corresponding Application PCT/IN2018/050112 dated Jun. 25, 2018, pp. 1-11.

Acharyya, S. et al., "Nanoclnsters of Cu (II) supported on Nano crystalline W (VI) oxide: a potential catalyst for single-step conversion of cyclohexane to adipic acid", published in Green Chem, 2015, 17, pp. 3490-3499.

Li, X. et al., "Selective alkane oxidation by manganese oxide: site isolation of MnOx Chains at the surface of MnWO4 nanorods" published in Angew Chem Int Ed Engl; 2016; 55(12); pp. 4092-4096.

Dai, Jing, et al., "Bifunctional H2WO4/TS-1 catalysts for direct conversion of cyclohexane to adipic acid: Active sites and reaction steps," published in Applied Catalysis B: Environmental; 2016; 192, pp. 325-341.

Zou, G., et al., "Oxidation of cyclohexane to adipic acid catalyzed by Mn-doped titanosilicate With hollow structure," published in Catalysis Communications; 2015, 58, pp. 46-52.

Wang, L. et al., "pH-controlled assembly of three-dimensional tungsten oxide hierarchical nanostrnctures for catalytic oxidation of cyclohexene to adipic acid," published in CrystEngComm, 2016,18, pp. 8688-8695.

Ghosh, S. et al., "Selective oxidation of cyclohexene to adipic acid over silver supported tungsten oxide nanostructured catalysts," published in Green Chem., 2014, 16, 2826-2834.

Acharyya S. et al., "Oxidation of Cyclohexene Over Nanoclnsters of Cu (II) Supported on Nanochrystalline Tungsten Oxide With H2O2 as Oxidant," published in Journal of Advanced Catalysis Science and Technology, 2014, 1, pp. 15-19.

* cited by examiner

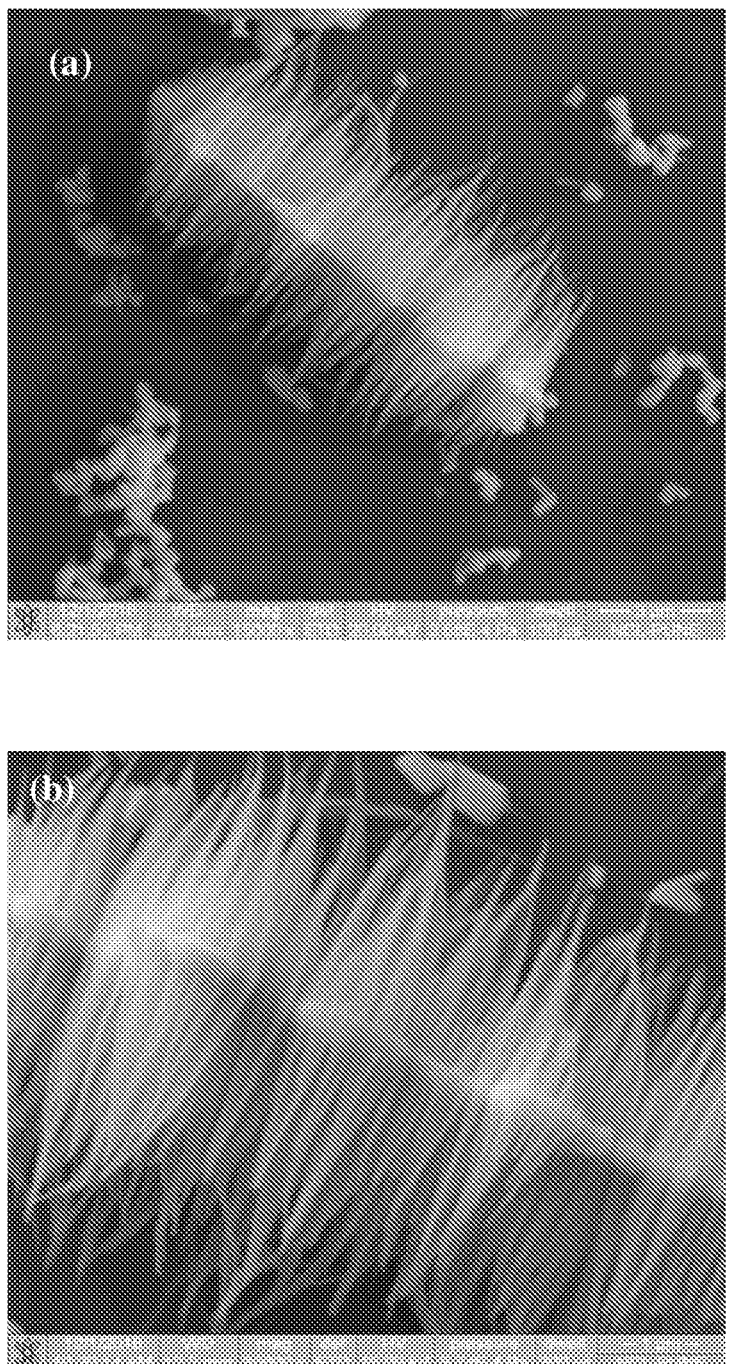
Fig: 1

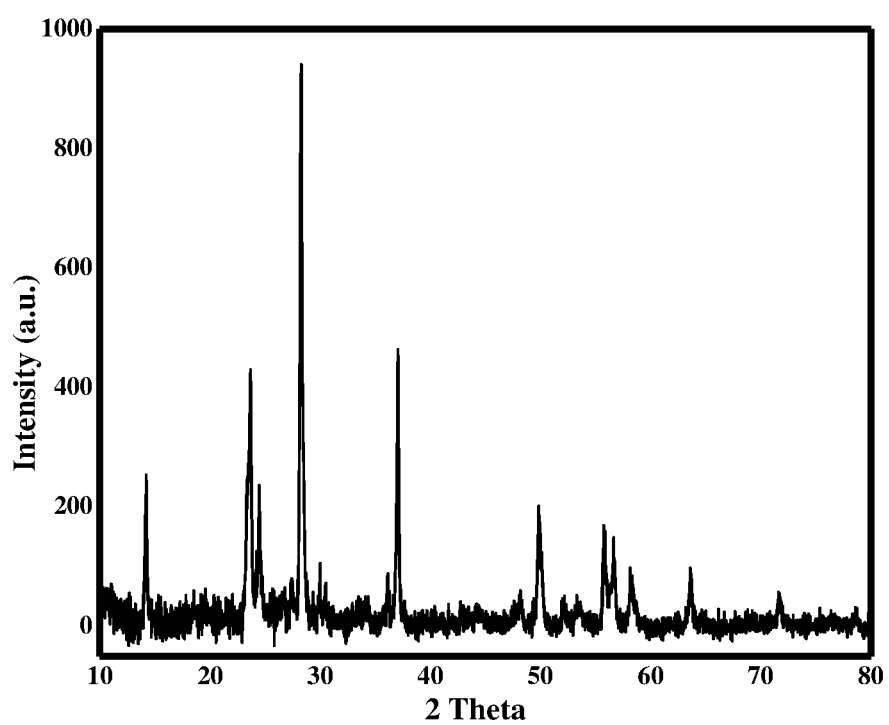
Fig: 2

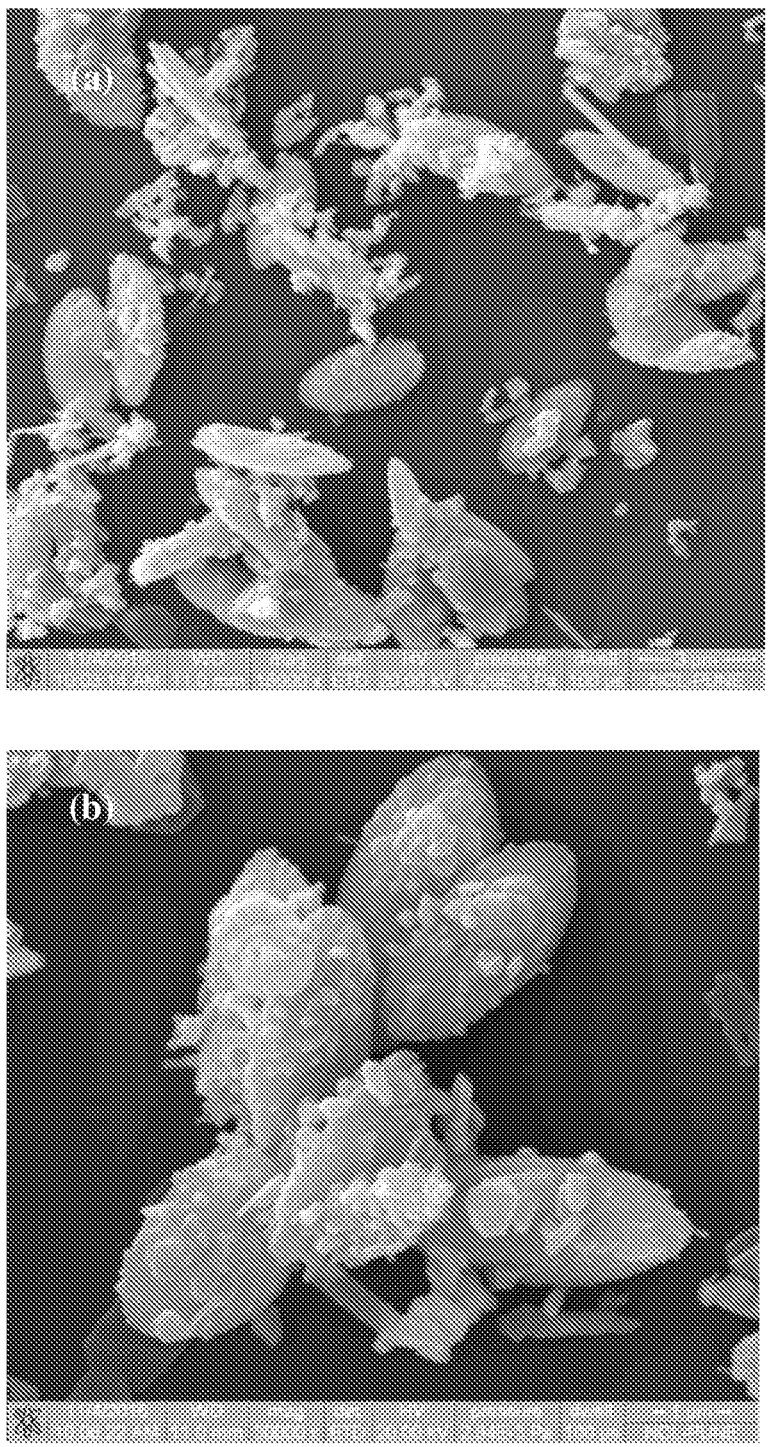
Fig: 3

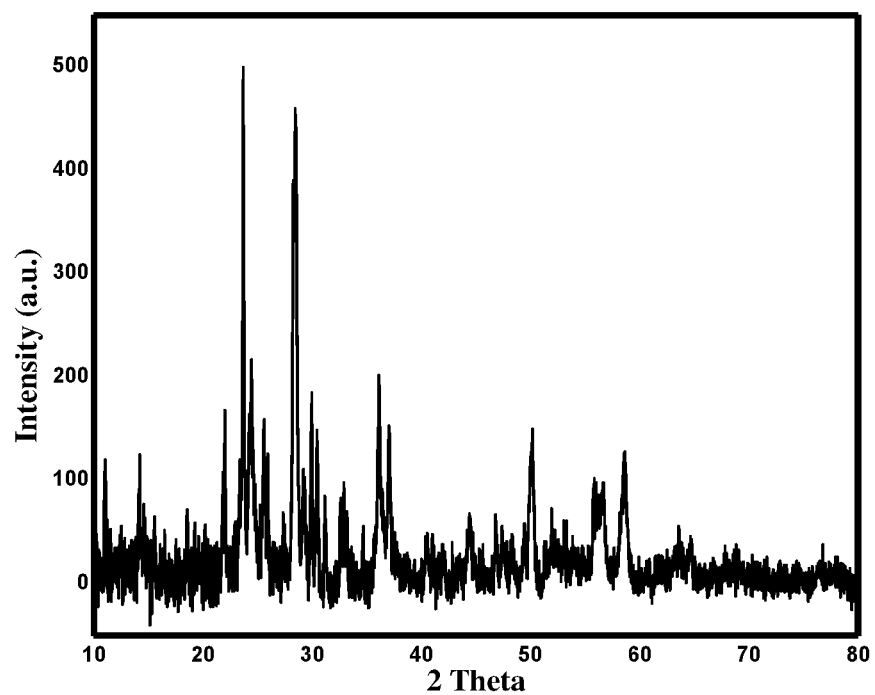
Fig: 4

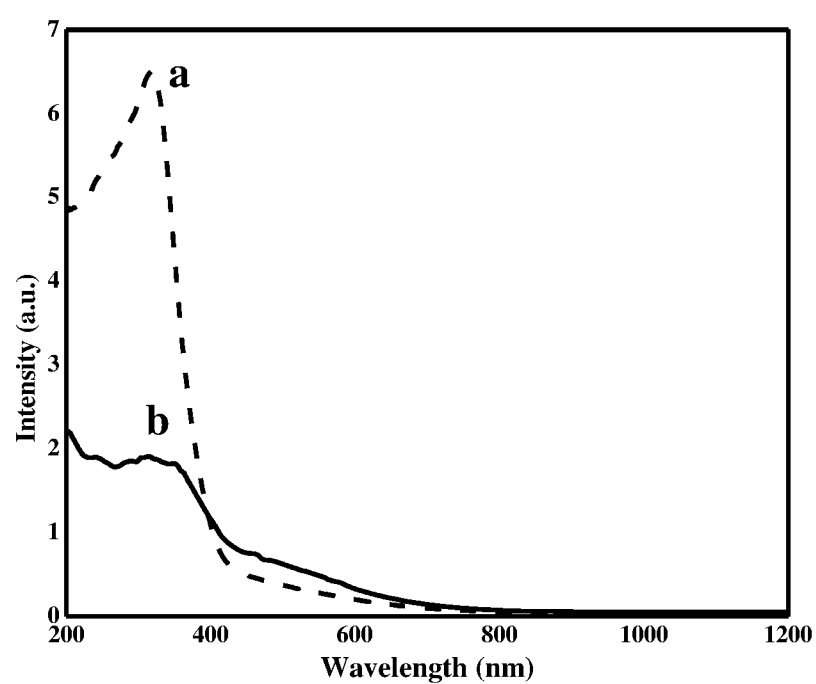
Fig: 5

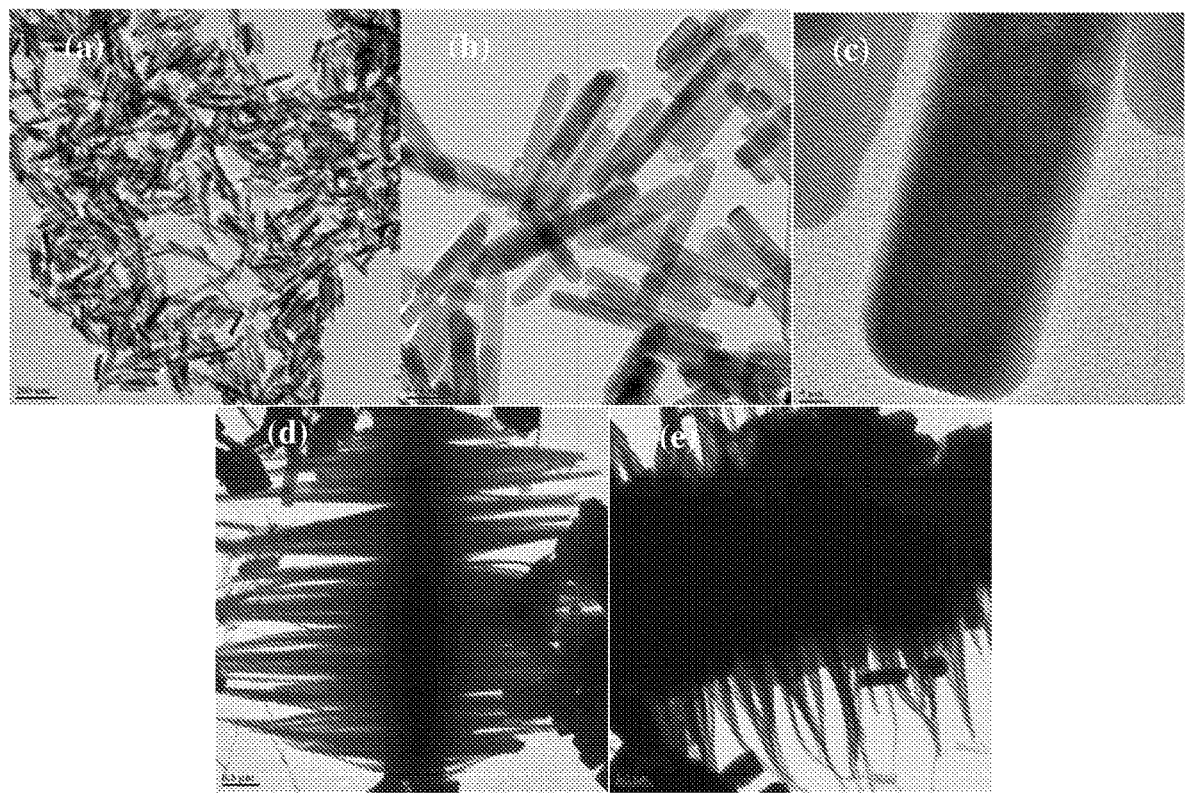
Fig: 6

SINGLE STEP PROCESS FOR THE OXIDATION OF CYCLOHEXANE

CROSS-REFERENCE TO RELATED PATENT APPLICATIONS

The present application is a U.S. national stage application under 35 U.S.C. § 371 of PCT Application No. PCT/IN2018/050112, filed Mar. 3, 2018, which claims priority to Indian Patent Application No. 201711007873, filed Mar. 7, 2017. The disclosures of the aforementioned priority applications are incorporated herein by reference in their entireties.

FIELD OF THE INVENTION

The present invention relates to a single step process for conversion of alkane to acid. More particularly, the present invention relates to a single step process for the conversion of cyclohexane to adipic acid by using manganese oxide, tungsten oxide or Mn—WOx nanostructure.

BACKGROUND AND PRIOR ART OF THE INVENTION

Adipic acid is a large volume commodity chemical used for the production of polymeric compounds. Cyclohexane can be used as a precursor for the manufacture of adipic acid. Generally, adipic acid from cyclohexane is made by a two step process. In the first step, cyclohexane is oxidized at a temperature range of 150 to 175° C. and a pressure of 115 to 175 psi in the presence of a soluble catalyst like cobalt napthenate or octoate in a concentration of 0.3 to 3 ppm. In the second step, the mixture of cyclohexanol and cyclohexanone, which are formed by the oxidation of cyclohexane in the first step, are oxidized by nitric acid to adipic acid. Sometimes, adipic acid is produced from a mixture of cyclohexanol and cyclohexanone called "KA oil", the abbreviation of ketone-alcohol oil. The KA oil is oxidized with nitric acid to give adipic acid, via a multistep pathway.

There are many drawbacks in the two-step process for the oxidation of cyclohexane to adipic acid used in commercial practice worldwide like yield is poor, use of cyclohexene or oxidants such as $H_2O_2$, low conversion of cyclohexane, large amounts (mole equivalent of nitric acid used) of nitrogen oxide vapors are released in the process which constitute an environmental hazard. Further, the current industrial process of adipic acid by using cobalt salt with air/conc. $HNO_3$ which needs high temperature (170° C.) and it also produces large amount of $NO_2$ as pollutant which causes global warming and ozone depletion. Also, the direct conversion of adipic acid from cyclohexane was mostly achieved by using $H_2O_2$ and TBHP as a vigorous oxidant. This process is not economical since these oxidants are required in large amount and are expensive. Also the main drawback of $H_2O_2$ is the ease of decomposing nature. So there is need to develop process for preparation of adipic acid without using $H_2O_2$.

In order to overcome drawbacks in the two step oxidation process, one step oxidation of cyclohexane has been tried over the years. Air is used as an oxidant in one step oxidation of cyclohexane. The catalysts mostly used in the oxidation of cyclohexane are cobalt and its mixture with other metals like iron. In the conventional methods, in-situ activation of the catalyst from cobaltous to cobaltic state is carried out with the help of activators like aldehydes and ketones.

U.S. Pat. No. 3,361,806 discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture. The drawback of this process is that it is a two step process for the conversion of cyclohexane to adipic acid as well as there is difficulty in the separation of cyclohexanol and cyclohexanone from the reaction mixture which makes the process expensive.

Article titled "Nanoclusters of Cu (II) supported on Nano crystalline W (VI) oxide: a potential catalyst for single-step conversion of cyclohexane to adipic acid" by S Acharyya et al. published in *Green Chem.*, 2015, 17, pp. 3490-3499 reports a facile hydrothermal synthesis method for the preparation of Cu (II) nanoclusters supported on a Nano crystalline W (VI) oxide catalyst with sizes between 35 and 65 nm.

Article titled "Oxidation of Cyclohexane Over Nanoclusters of Cu (II) Supported on Nanocrystalline Tungsten Oxide with $H_2O_2$ as Oxidant" by SS Acharyya et al. published in *Journal of Advanced Catalysis Science and Technology;* 2014, 1, pp 15-19 reports a facile hydrothermal synthesis method is developed for the preparation of Cu (II) nanoclusters (with average particle size 6 nm) supported on nanocrystalline tungsten (VI) oxide. The good catalytic activity is shown for the single step conversion of cyclohexane to adipic acid using $H_2O_2$, exhibiting 62.5% cyclohexane conversion and 27% selectivity towards adipic acid at room temperature. The catalyst can be reused several times without any activity loss, which is a prerequisite for practical application.

Article titled "Selective alkane oxidation by manganese oxide: site isolation of $MnO_x$ chains at the surface of $MnWO_4$ nanorods" by X Li et al. published in *Angew Chem Int Ed Engl.;* 2016; 55(12); pp 4092-4096 reports a catalytically inactive solid, such as $MnWO_4$, can be converted into a highly active and selective catalyst by knowledge-based synthesis. Hydrothermal techniques guided by in situ spectroscopy were applied to control the surface termination.

Articled titled "Bifunctional $H_2WO_4$/TS-1 catalysts for direct conversion of cyclohexane to adipic acid: Active sites and reaction steps" by Jing Dai et al. published in *Applied Catalysis B: Environmental;* 2016; 192, pp 325-341 reports a hollow $H_2WO_4$/TS-1 bifunctional catalyst with excellent catalytic activity for the direct transformation of cyclohexane to adipic acid with 30% hydrogen peroxide by a non-$HNO_3$ route. The main drawback of this process is low conversion (31%). Further, the separation of cyclohexane from the reaction products is very difficult and reuse of that unreacted cyclohexane makes the process expensive.

Article titled "Oxidation of cyclohexane to adipic acid catalyzed by Mn-doped titanosilicate with hollow structure" by G Zou et al. published in *Catalysis Communications;* 2015, 58, pp 46-52 reports that one-step oxidation of cyclohexane to adipic acid (AA) was carried out at 413 K over manganese-doped titanium silicalite with hollow structure (HTS) using oxygen as oxidant without any initiator or solvent. The catalyst exhibited high conversion (13.4%) and reasonable product (AA) selectivity (57.5%). Hot-separation and catalyst-recycle tests proved that the catalyst acted as a heterogeneous one and it could be reused four times without losing its activity.

Article titled "pH-controlled assembly of three-dimensional tungsten oxide hierarchical nanostructures for catalytic oxidation of cyclohexene to adipic acid" by L Wang et al. published in *Cryst Eng Comm*, 2016,18, pp 8688-8695 reports a facile pH-controlled strategy for synthesizing three-dimensional tungsten oxide architectures with different morphologies without using any templates or surfactants. These hierarchical architectures with rod-like, disk-like and sphere-like morphologies are assembled from one-dimensional tungsten oxide nanowires/nanorods.

Article titled "Selective oxidation of cyclohexene to adipic acid over silver supported tungsten oxide nanostructured catalysts" by S Ghosh et al. published in *Green Chem.*, 2014, 16, 2826-2834 reports a new synthesis strategy to prepare 5 nm metallic silver nanoparticles (AgNPs) supported on tungsten oxide (WO3) nanorods with diameters between 40 and 60 nm in the presence of a cationic surfactant, cetyltrimethylammonium bromide (CTAB).

The prior art processes for the synthesis of adipic acid suffer from the drawbacks such as low yield, low selectivity towards desired product, two step process, decomposing nature of peroxides, expensive, corrosive chemicals used and difficulty in removing the side products. Therefore, to avoid prior art drawbacks there is need for simple, economic, environment friendly process for the synthesis of adipic acid from cyclohexane. Accordingly, the present invention provides a simple process for the synthesis of adipic acid from cyclohexane having improved yield and carried out under environmentally benign conditions.

OBJECTS OF THE INVENTION

The main objective of the present invention is to provide a single step process for the conversion of alkane to acid in presence of manganese oxide, tungsten oxide or Mn—WOx nanostructure as a catalyst.

Another objective of the present invention is to provide a single step process for the conversion of cyclohexane to adipic acid in presence of manganese oxide, tungsten oxide or Mn—WOx nanostructure as a catalyst.

Yet another objective of the present invention is to provide a process for the preparation of Mn with Tungsten oxide fish bone catalyst.

SUMMARY OF THE INVENTION

Accordingly, the present invention provides a single step process for the conversion of cyclohexane to adipic acid, wherein the process comprises addition of cyclohexane, solvent and catalyst to a reactor followed by charging oxygen with pressure in the range of 0-30 bars at a temperature ranging from 100-125° C. under constant stirring for a period in the range of 5 to 6 hours to afford adipic acid, wherein said catalyst is selected from manganese oxide, tungsten oxide or Mn—WOx nanostructure and the yield of adipic acid is in the range of 20-40%.

In preferred embodiment, the Mn—WOx nanostructure catalyst is in the form of nanorod, nanoseed or fish bone structure.

In more preferred embodiment, the Mn—WOx nanostructure catalyst is in the form of fish bone structure.

The selectivity of said reaction toward adipic acid is in the range of 40 to 70%.

The solvent is selected from acetonitrile, acetic acid, water or mixture thereof.

In an embodiment, the present invention provides a process for the preparation of Mn with Tungsten oxide fish bone catalyst comprising the steps of:
 a) dissolving sodium tungstate dihydrate, manganese (II) sulfate monohydrate and metal sulphates in a suitable solvent at a temperature ranging from 25-30° C.;
 b) adjusting the pH of solution of step (a) upto 0.5 to 5 by constant stirring for 30-50 mins;
 c) heating the solution of step (b) at a temperature ranging from 100-250° C. for a time period ranging from 24-72 hours;
 d) cooling the solution of step (c) upto 25-30° C. to afford Mn with Tungsten oxide fish bone catalyst.

In preferred embodiment, the metal sulphate is selected from sodium sulfate, potassium sulfate or mixture thereof.

ABBREVIATION

Mn—Manganese
W—Tungsten
RPM—Rotations per minute
$Na_2WO_4 \cdot 2H_2O$—Sodium Tungstate dihydrate
$Na_2SO_4$—Sodium sulfate
$K_2SO_4$—Potassium sulfate
$MnSO_4 \cdot H_2O$—Manganese (II) Sulfate Monohydrate
$Mn(NO_3)_2 \cdot 4H_2O$—Manganese (II) Nitrate Tetrahydrate
$HNO_3$—Nitric acid
NaOH—Sodium Hydroxide
KA oil—(cyclohexanone and cyclohexanol)

BRIEF DESCRIPTION OF THE DRAWINGS

FIG. 1: SEM images of Mn—WOx fish bone structure
FIG. 2: XRD—pattern for Mn—WOx fish bone structure
FIG. 3: SEM images of Mn—WOx nano seed structure
FIG. 4: XRD—pattern for nano seed structure
FIG. 5: UV-Visible spectra of (a) seeds and (b) fish bone structure
FIG. 6: TEM images of Mn—$WO_4$ nano rods and Mn—WOx fish bone structures

DETAILED DESCRIPTION OF THE INVENTION

The invention will now be described in detail in connection with certain preferred and optional embodiments, so that various aspects thereof may be more fully understood and appreciated.

In view of the above, the present invention provides an economic, environment friendly, single step process for the oxidation of cyclohexane to adipic acid in presence of catalyst selected from manganese oxide, tungsten oxide or Mn—WOx nanostructure.

In an embodiment, the present invention provides a single step process for the conversion of cyclohexane to adipic acid, wherein the process comprises addition of cyclohexane, solvent and catalyst to a reactor followed by charging oxygen with pressure in the range of 0-30 bars at a temperature ranging from 100-125° C. under constant stirring for a period in the range 5 to 6 hours to afford adipic acid.

The catalyst is selected from manganese oxide, tungsten oxide or Mn—WOx nanostructure. In preferred embodiment, the catalyst is Mn—WOx nanostructure. In more preferred embodiment, the Mn—WOx nanostructure catalyst is in the form of nanorod, nanoseed or fish bone structure.

The yield of adipic acid is in the range of 20-40%. In preferred embodiment, the yield of adipic acid is in the range of 35-40%. The solvent is selected from acetonitrile, acetic acid and water.

The selectivity of the process of instant invention is in the range of 40 to 70%. In a preferred embodiment, the selectivity of the process of instant invention is in the range of 45 to 60%.

In another embodiment, the present invention provides a process for the preparation of Mn with Tungsten oxide fish bone catalyst comprising the steps of:

a) dissolving metal tungstate, manganese (II) sulfate monohydrate and metal sulphates in a suitable solvent at a temperature ranging from 25-50° C.;
b) adjusting the pH of solution of step (a) upto 0.5-5 by constant stirring for 30-50 mins;
c) heating the solution of step (b) at a temperature ranging from 100-250° C. for a time period ranging from 24-72 hours;
d) cooling the solution of step (c) upto 25-30° C. to afford Mn with Tungsten oxide fish bone catalyst.

In preferred embodiment, said metal tungstate is selected from sodium tungstate dihydrate.

In another preferred embodiment, said metal sulphate is selected from sodium sulfate, potassium sulfate or mixture thereof.

The mole ratio of Tungsten to Manganese is in the range of 0.1:0.005-0.1:0.1.

The solvent of step (a) is selected from milli-Q water/alcohol/water-alcohol mixture.

The single step process for the conversion of cyclohexane to adipic acid is as depicted in scheme 1 below. The scheme 1 shows cyclohexane to adipic acid over Mn—W Nano structures oxygen as an oxidant.

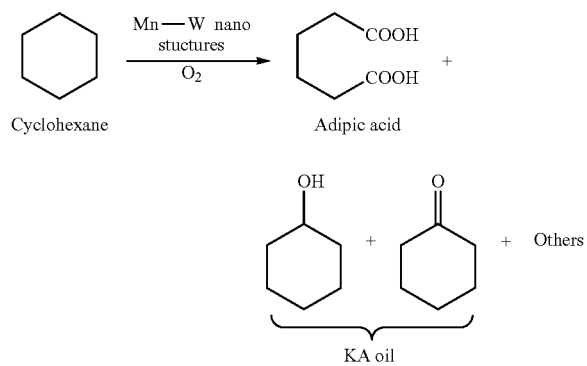

Scheme: 1

The following table 1 shows oxidation of cyclohexane to adipic acid for reaction conditions; catalyst amount: 50 Mg, Cyclohexane: 6 ml, Acetonitrile: 3 ml, Temperature: 125° C., Oxygen pressure: 30 bar, Time: 6 hours.

TABLE 1

| Sr. No. | Catalyst | Conversion of cyclohexane (%) | Selectivity of ka oil (%) | Selectivity of adipic acid (%) | Yield of ka oil (%) | Yield of adipic acid (%) |
| --- | --- | --- | --- | --- | --- | --- |
| 1 | Tungsten oxide fish bone alone | 42.7 | 13.26 | 55.64 | 5.70 | 23.91 |
| 2 | Tungsten oxide alone | 24.75 | 16.19 | 51.03 | 4.00 | 12.60 |
| 3 | Manganese oxide alone | 40.69 | 1.79 | 58.70 | 0.73 | 23.16 |
| 4 | Mn—WOx fish bone structure | 63.33 | 7.48 | 59.1 | 4.74 | 37.4 |
| 5 | Mn—WO$_4$ Nano rods | 32.58 | 23.23 | 48.49 | 7.56 | 15.79 |
| 6 | Mn-WOx Nano seeds | 31.77 | 22.00 | 52.60 | 6.99 | 16.68 |

The following table 2 shows catalyst and adipic acid yield over various Mn—W nanostructures. Reaction conditions; catalyst amount: 50 Mg, Cyclohexane: 6 ml, Acetonitrile: 3 ml, Temperature: 125° C., Oxygen pressure: 30 bar, Time: 6 hours.

TABLE 2

| Catalyst | Yield in % |
| --- | --- |
| W oxide | 23.91 |
| Mn oxide | 23.16 |
| Mn—WOx fish bone | 37.40 |
| Mn WO$_4$ nano rods | 15.79 |
| Mn WOx nano seeds | 16.68 |

From above data it is shown that Mn—WOx fish bone structure is giving high percentage of yield around 40% compared to other nano structures like rods, seeds. Fish bone structure is playing crucial for selective oxidation of adipic acid.

FIG. 1 represents SEM images of Mn—WOx nanostructures [(a) and (b)] which are prepared from 7 mmol of Na$_2$WO$_4$. 2H$_2$O using 1.8 mmol of Sodium and potassium salt and MnSO$_4$.H$_2$O, in case of Example 1.

FIG. 2 represents XRD pattern of Mn—WOx nanostructures which are prepared from 7 mmol of Na$_2$WO$_4$. 2H$_2$O using 1.8 mmol of Sodium and potassium salt and MnSO$_4$.H$_2$O, in case of Example 1.

FIG. 3 represents SEM images [(a) and (b)] of Mn—WOx nanostructures which are prepared from 7 mmol of Na$_2$WO$_4$. 2H$_2$O using 1.8 mmol of Na$_2$SO$_4$ Sodium and potassium salt, in case of Example 1. Different nanostructures of Mn—WOx are achieved by changing the reaction parameter, in case of Example 1.

FIG. 4 represents XRD pattern of Mn—WOx nano seed structures which are prepared from 7 mmol of Na$_2$WO$_4$. 2H$_2$O using 1.8 mmol of Sodium and potassium salt and MnSO$_4$.H$_2$O, in case of Example 1. Different nanostructures of Mn—WOx are achieved by changing the reaction parameter, in case of Example 1.

FIG. 5 represent absorption spectra of Mn—WOx (a) seeds and (b) fish bone structure.

FIG. 6 represent TEM images of Mn—WO$_4$ nano rods structure [(a) to (c)] in case of Example 2 and Mn—WO fish bone structure [(d) to (e)] in case of Example 1.

EXAMPLES

Following examples are given by way of illustration therefore should not be construed to limit the scope of the invention.

Example 1

Mn—W (Fishbone) Synthesis Procedure

In a typical experiment, 7 mmol of $Na_2WO_4 \cdot 2H_2O$, 1.8 mmol of $Na_2SO_4$ and 1.8 mmol of $K_2SO_4$ and $MnSO_4 \cdot H_2O$ was used. Tungsten to Manganese mole ratio should be 1:0.01 0.1:0.005-0.1:0.1 were dissolved in milli-Q water at 25° C. Under constant stirring, pH of the solutions were then adjusted to 2.25. Then stirred at 30-50 minutes. The solution was added to Teflon-lined stainless steel autoclave and heated at 180° C. for 24 hours in a hot air oven and cooled to room temperature naturally. The products were collected by vacuum filtration and washed repeatedly with milli-Q water and ethanol and dried under vacuum at 60° C. for 5 hours. After this calcination was done at 550° C. for 4 hr.

Example 2

Mn—W Nano Rods Synthesis Procedure

Mn—W Nanorods structure prepared by hydrothermal synthesis. 0.2M solution of $Mn (NO_3)_2 \cdot 4 H_2O$ and 0.2M solution of $Na_2WO_4 \cdot 2H_2O$ added in 50 ml of milli-Q water to a mixed solution of pH=6.7. Subsequently, the pH of the mixed solution was adjusted to 9.9 by adding appropriate amounts of 0.1 M $HNO_3$ or 0.1 M NaOH and the mixtures were transferred to the autoclave and the temperature was raised from 20° C. to 180° C. at a rate of 5° C./min. The synthesis temperature was kept at 180° C. for 12 hours. Then collected catalyst was calcined at 500° C. for 6 hours.

Example 3

Oxidation of Cyclohexane

Liquid phase oxidation of cyclohexane was carried out in 50 ml autoclave Parr reactor using 50 mg of catalysts, 3 ml of Acetonitrile solvent and 6 ml of cyclohexane which were introduced in to reactor. Oxygen was charged to 30 bars, and temperature maintained at 125° C. under stirring 550 RPM for 6 hours. After reaction, the mixture was cooled down to room temperature and the product was collected from reaction mixture, dissolved in 7:3 ratio of acetone and water. The product was analyzed through by HPLC connected with C18 column and 0.005M $H_2SO_4$ and water used as a mobile phase. The yield were calculated and normalized with respect to HPLC response factor. The reusability of the catalyst was tested for multiple cycles after recovering the catalyst and washing with acetone and then with water several times.

The following table shows oxidation of cyclohexane to adipic acid for Reaction conditions; catalyst amount: 50 Mg, Cyclohexane: 6 ml, Acetonitrile: 3 ml, Temperature: 125° C., Oxygen pressure: 30 bar, Time: 6 hours

| Sr. No. | Catalyst | Conversion of cyclohexane (%) | Selectivity of ka oil (%) | Selectivity of adipic acid (%) | Yield of ka oil (%) | Yield of adipic acid (%) |
|---|---|---|---|---|---|---|
| 1 | Tungsten oxide fish bone alone | 42.7 | 13.26 | 55.64 | 5.70 | 23.91 |
| 2 | Tungsten oxide alone | 24.75 | 16.19 | 51.03 | 4.00 | 12.60 |
| 3 | Manganese oxide alone | 40.69 | 1.79 | 58.70 | 0.73 | 23.16 |
| 4 | Mn—WOx fish bone structure | 63.33 | 7.48 | 59.1 | 4.74 | 37.4 |
| 5 | Mn—WO$_4$ Nano rods | 32.58 | 23.23 | 48.49 | 7.56 | 15.79 |
| 6 | Mn—WOx Nano seeds | 31.77 | 22.00 | 52.60 | 6.99 | 16.68 |

Example 4

Self-assembling of $WO_3$ and $W_{18}O_{49}$ Nanorods Networks Leading to Nanorods Bundles, Cocoon, Urchin, Fishbone and Few Other Patterns In a typical experiment 7 mmol of $Na_2WO_4$, 1.8 mmol of $Na_2SO_4$ and 1.8 mmol of $K_2SO_4$ were dissolved in milli Q water at room temperature. Under constant stirring, pH of the solutions was then adjusted by dropwise addition of diluted HCL. The solution color changes from colorless to light to darker yellow with decreasing pH. After stirring for additional 30 minutes, the solution was added to 30 ml of Teflon-lined stainless steel autoclave and heated at 180° C. for 24 hours in a hot air oven and cooled to room temperature naturally. The products (bluish green to light green color) were collected by vacuum filtration and washed repeatedly with milli Q water and ethanol and dried under vacuum at 60° C. for 5 hours.

Advantages of the Invention

1. Economical single step process for preparation of Adipic acid from cyclohexane.
2. Eco-benign production of adipic acid using oxygen as an oxidant over Mn—W nano structures in absence of production of any harmful gases like $NO_2$ etc.
3. Catalyst synthesis strategy has the advantages that it is one step hydrothermal method, aqueous medium based and requires no surfactant or stabilizing agent or conventional template. Furthermore, it also affords self-assemble of 1D nanorods of Mn—WO into hierarchical fishbone type nanostructure.

4. The high percentage of yield of catalyst is obtained at very low temperature.

5. Decomposition of Adipic acid is avoided.

The invention claimed is:

1. A single step process for conversion of cyclohexane to adipic acid, the process comprising: adding cyclohexane, a solvent and a catalyst to a reactor followed by charging oxygen with a pressure in a range of 0-30 bars at a temperature ranging from 100-125° C. under constant stirring for a period in a range of 5 to 6 hours to afford adipic acid, wherein the catalyst is Mn-WOx nanostructure, wherein the Mn-WOx nanostructure catalyst is in the form of a nanorod, a nanoseed or a fish bone structure, and wherein yield of adipic acid is in a range of 20-40%.

2. The process as claimed in claim 1, wherein said solvent is selected from acetonitrile, acetic acid, water or a mixture thereof.

3. The process as claimed in claim 1, wherein the Mn-WOx nanostructure catalyst is in the form of a fish bone structure.

4. The process as claimed in claim 1, wherein selectivity of the process towards adipic acid is in a range of 40 to 70%.

5. A process for the preparation of Mn with Tungsten oxide fish bone catalyst, the process comprising the steps of:
   a) dissolving sodium tungstate dihydrate, manganese (II) sulfate monohydrate and metal sulphates in a suitable solvent at a temperature ranging from 25-30° C. to form a solution;
   b) adjusting the pH of the solution of step (a) up to 0.5 to 5 by constant stirring for 30-50 mins;
   c) heating the solution of step (b) at a temperature ranging from 100-250° C. for a time period ranging from 24-72 hours;
   d) cooling the solution of step (c) up to 25-30° C. to afford Mn with Tungsten oxide fish bone catalyst.

6. The process as claimed in claim 5, wherein the metal sulphate is selected from sodium sulfate, potassium sulfate or a mixture thereof.

7. The process as claimed in claim 5, wherein the solvent is selected from water, an alcohol or a mixture thereof.

\* \* \* \* \*